US00PP20325P3

(12) United States Plant Patent
James

(10) Patent No.: US PP20,325 P3
(45) Date of Patent: Sep. 22, 2009

(54) VARIETY OF ROSE PLANT NAMED 'PEJAMBLU'

(50) Latin Name: *Rosa*
Varietal Denomination: Pejamblu

(76) Inventor: Peter James, 324 City Road, Tividale, Oldbury, West Midlands (GB), B691QP ( * ) Notice: Subject to any disclaimer, the term of this patent is extended or adjusted under 35 U.S.C. 154(b) by 38 days.

(21) Appl. No.: 11/708,881

(22) Filed: Feb. 21, 2007

(65) Prior Publication Data

US 2008/0148436 P1 Jun. 19, 2008

(30) Foreign Application Priority Data

Dec. 19, 2006 (EM) ..... 2006/2570

(51) Int. Cl.
*A01H 5/00* (2006.01)

(52) U.S. Cl. ..... Plt./148

(58) Field of Classification Search ..... Plt./130, Plt./149

See application file for complete search history.

*Primary Examiner*—Kent L Bell
(74) *Attorney, Agent, or Firm*—Fulwider Patton LLP

(57) ABSTRACT

A new and distinct cultivar of Rose plant named 'Pejamblu' is characterized in compact upright bush having a mauve/lilac color flowers ageing to a slate blue and having a strong pleasant fragrance. The plant also benefits from a lengthy flowering period of repeated flowerings between spring and fall. The plant is tolerant of dry conditions and exhibits tolerance to Black Spot and Powdery mildew, Rust mildew, and Downey mildew.

4 Drawing Sheets

BACKGROUND OF THE NEW PLANT

The present invention relates to a new and distinct cultivar of Rose, species Rosa, and further known by the varietal name 'Pejamblu.' This new variety is also sold under the Breeder's reference name PEJAMBLU. The new variety was discovered through selective cross-pollination initiated in June 2000. The seed parent is known as "Rose 'NATURAL BEAUTY' (ROGSCRIV)", a pink/apricot colored rose having double 26–40 petals of a 75 mm rosette borne on small clusters. No patent is known by the inventor to cover the parental seed. The pollen parent seedling was derived from a cross of SUMMER WINE and SCRIVBELL. PEJAMBLU has a unique mauve/lilac flower ageing to slate blue, with semi-double 12–16 petals and 75–100 mm flowers. The derivation by cross pollination occurred at 324 City Road, Tividale, Oldbury, West Midlands, United Kingdom B691QP. The first asexual reproduction occurred at the breeder Peter James' home at 324 City Road, Tividale B691QP, Oldbury West Midlands, U.K. Plants were budded on to Lasca under stock and proved to be true to type when grown over several generations and all have been stable. Propagation by cuttings in Australia has also proved stable, and the desirable features of the plant have remained constant throughout the evaluation period. The evaluation of the variety was carried out at Warner Roses of Shropshire. U.K. TF109EP.

SUMMARY OF THE INVENTION

Plants of the new Rose variety can be compared to other plants of its genus. 'Pejamblu' is characterized by its coloring, its abundant dark green foliage, its strong pleasant fragrance, and its abundant flowers. The variety is distinct in its flower color, mauve fading to slate blue, appearing very blue under normal climatic conditions. The variety has a very strong sweet citrus fragrance, and the foliage is plentiful and semi-malt in appearance. The habit of 'Pejamblu' is medium height and compact bushing as opposed to spreading, and it possesses a larger flower size and multiple flowerings between Spring and Fall.

DESCRIPTION OF THE DRAWING

The accompanying colored photographs illustrate the new cultivar.

DETAILED BOTANICAL DESCRIPTION OF THE NEW PLANT

Figure 1:
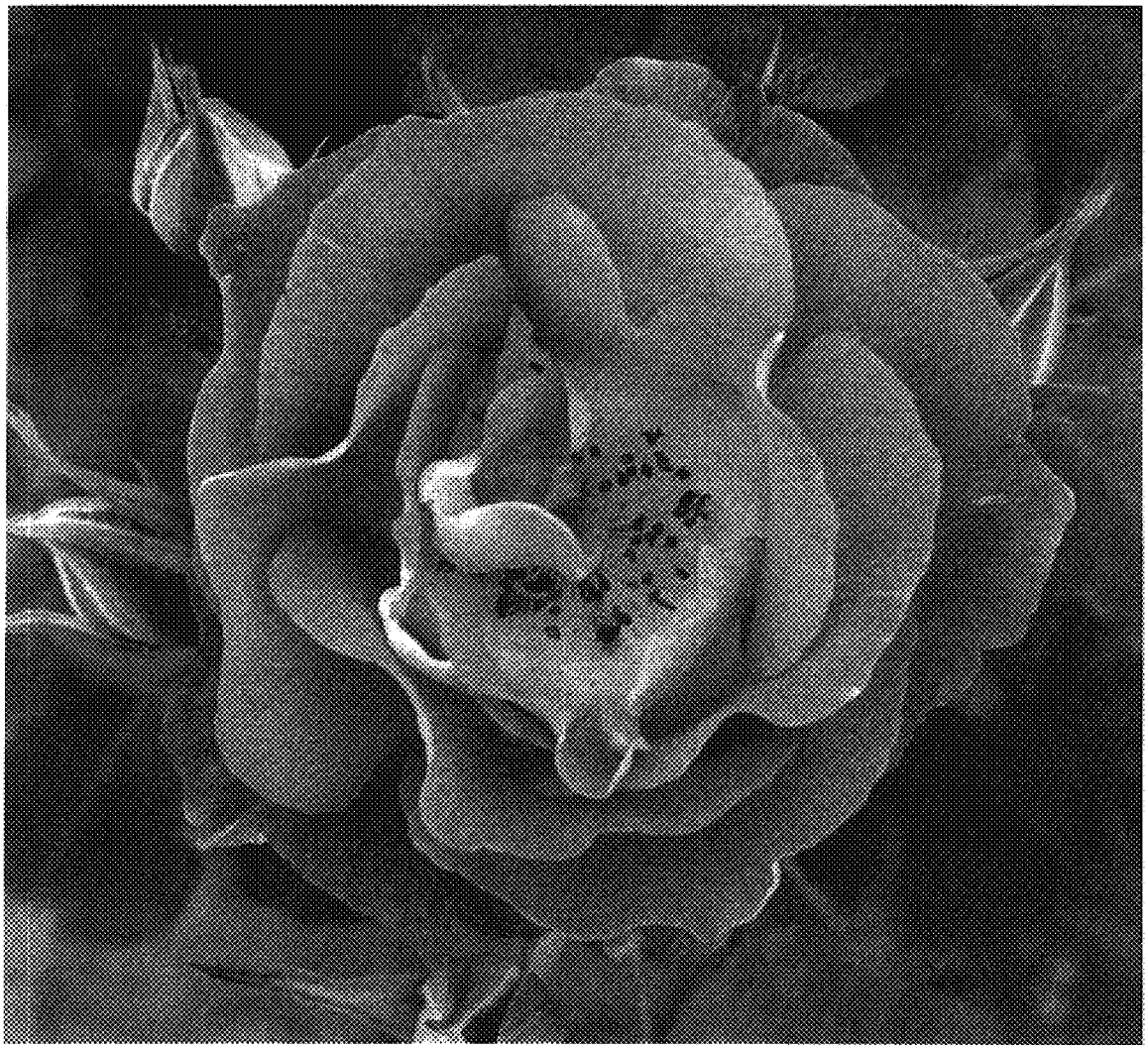
FIG. 1 shows an enlarged view of the flower.
Figure 2:
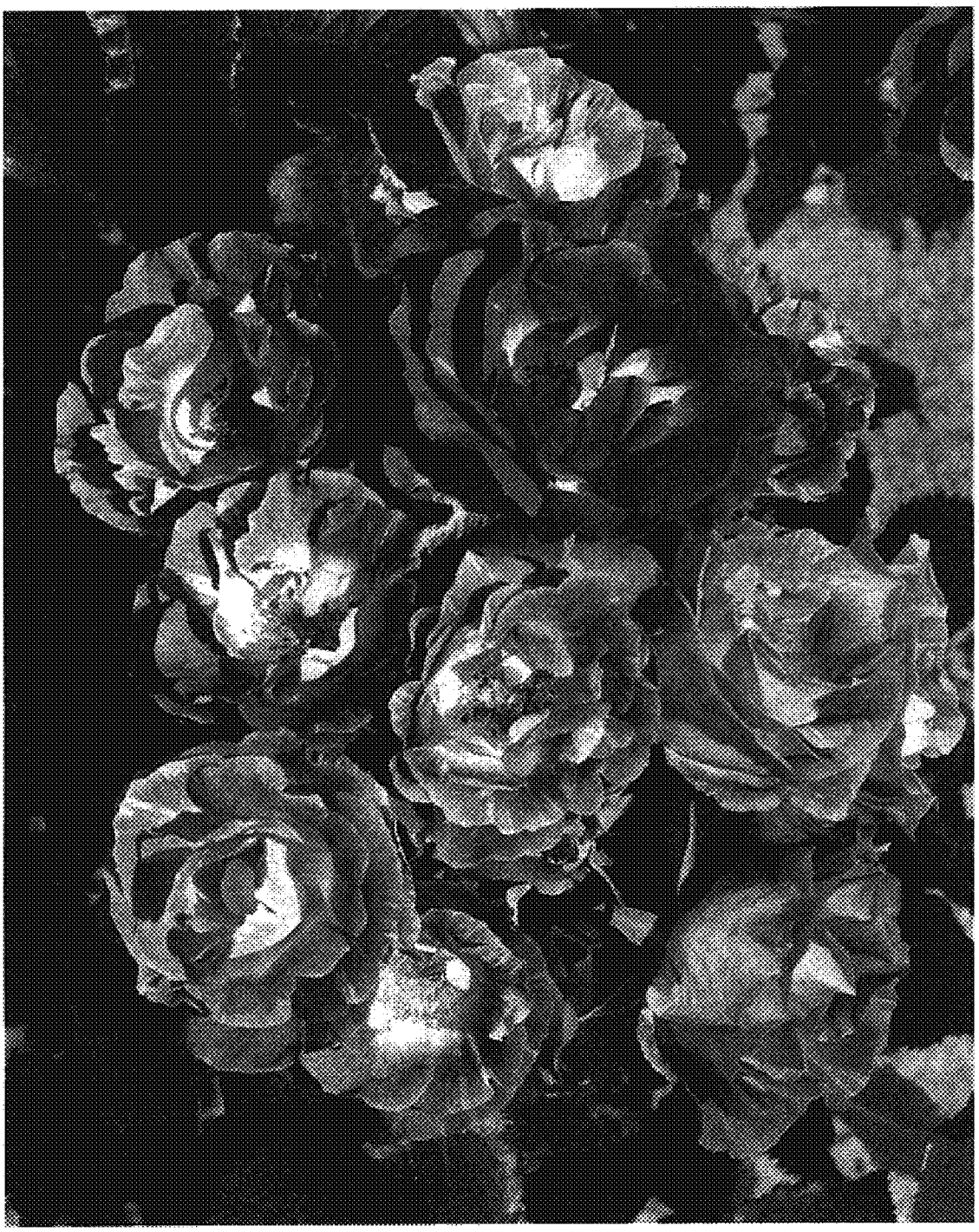
FIG. 2 shows a cluster of flowers in various stages of growth and illustrates a progression of color from mauve/lilac to slate blue.
Figure 3:
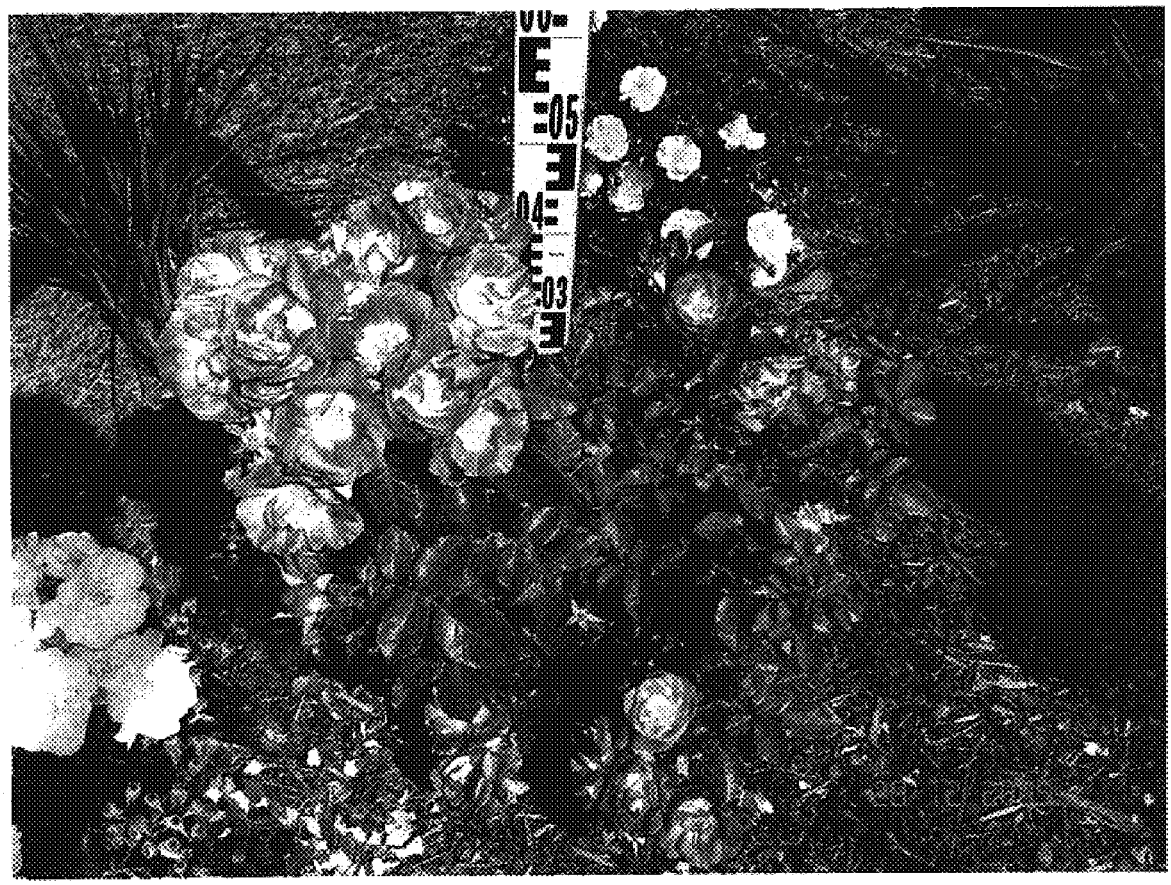
FIG. 3 shows a mature plant with several clusters of flowers.
Figure 4:
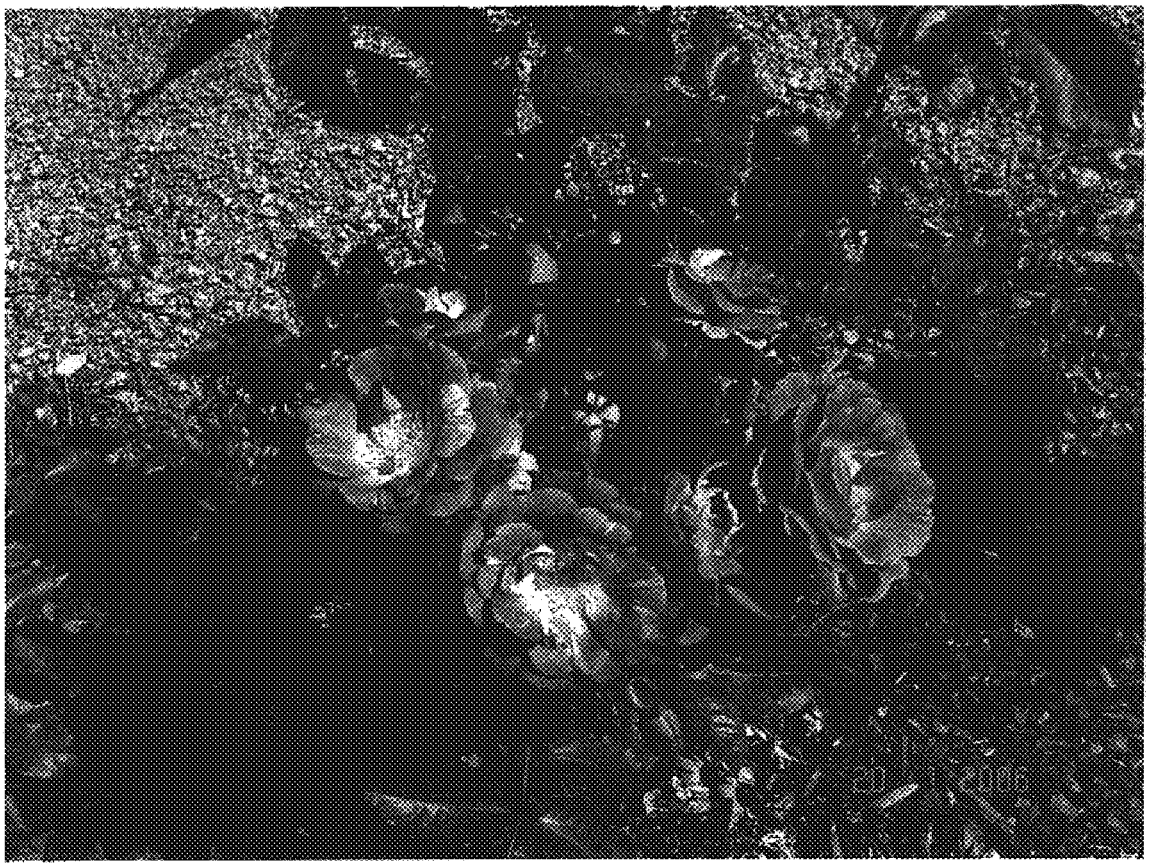
FIG. 4 shows a closer view of the flowers and foliage of the new rose.

The following detailed description sets forth characteristics of the new cultivar. In the following table of comparative features, color references are made to The Royal Horticultural Society of London Colour Chart, 1995 Edition. The color values were determined on plant material grown at 327 Monbulk Road, Silvan, Victoria, 3795 Australia.

| Characteristic | Measurement |
|---|---|
| Genus | Rose |
| Species | hybrid |
| Plant Characteristics | |
| Plant Density | Medium density typical of Floribunda rose |
| Plant Growth Type | Compact upright bush |
| Plant Height (mm) | 900-1200 mm |
| Plant Width (mm) | 800 mm |
| Stem Diameter (mm) | 6-10 mm |

-continued

| Characteristic | Measurement |
|---|---|
| Leaf Characteristics | |
| Leaf Color | Dark matte green, Green Group 139A; semi-glossy upper surface |
| Leaf Length (mm) | 90 mm |
| Leaf Width (mm) | 58 mm |
| Flower Characteristics: Pedicel prickles | Very few small prickles on pedicel |
| Bud shape (ovate, round) | Ovate, 30 mm × 14 mm |
| Flower Size | 80 mm diameter |
| Flower profile upper (flattened, flat) | Flat |
| Flower profile lower (flattened convex, flat) | Flat |
| Inflorescence Type | Indeterminate, cluster of 15 or more flowers |
| Sepal | 5 arching down from petals in open flower |
| Number of petals (13-26, 26-50, over 50) | 13-26 |
| Petal Size (small, large) | Medium |
| Petal Width (mm) | 42 mm wide |
| Petal Length (mm) | 45 mm long |
| Petal Arrangement (overlapping, not touching) | Overlapping |
| Pedicel Length (mm) | 44 mm |
| Number of flowers | Abundant flowers, 15 to 20 per stem cluster |
| Time of Flowering (med, early, late) | Early spring |
| Length of Flowering Period (med, long) | Long, early spring to late fall |
| Color midzone outside (RHS) | Purple group 76D |
| Color midzone inside (RHS) | Violet group 83B |
| Color margin inside | Violet group 83B |
| Color basal spot | Purple group 76D |
| Filament color | Yellow Group 11D |
| Anther | Greyed-Orange Group 165B |
| Style color | Yellow Group 11D |
| Seed Vessel Characteristics: | Medium to large |
| Color (green, ND, green and purple) | Green, Green Group 138A |
| Method of Breeding | Selective cross pollination |
| Parent Seedling | Natural Beauty 'Rogscriv' × Seedling |
| Growth Rate | Medium to fast growth rate. Flowers in first year at 70-90 cm in height.<br>Several flower flushes from early spring to late fall<br>Individual flowers last 7-10 days |
| Leaf Characteristics | Leaves abundant, compound 5 leaflets, sometimes 7 leaflets.<br>Dark green, Green Group RHS 139A on upper surface and RHS 138 B on lower surface.<br>Ovate, margin finely serrated, upper leaf surface smooth shiny, lower leaf surface matte. |
| Bracts, Pedicle and Peduncle | 2 bracts, lower surface Yellow-Green Group RHS 146C, upper surface RHS 137A with centre longitudinal stripe Greyed-Red Group RHS 182A<br>Pedicel Yellow-Green Group RHS 146C, 44 mm in length<br>Peduncle Yellow-Green Group RHS 146A 19 to 28 mm in length |
| Umbels per plant | Cluster of 15 or more flowers. |
| Flower buds | Medium bud - 8 mm diameter<br>Pointed and tapering<br>Near color Yellow Green Group RHS 146A<br>Opens as tight bud, ageing to flat flower with petals fully open and sepals folding back and pointing down away from the flower |
| Reproductive Organs | Numerous stamens and pollen<br>Anther color: Greyed-Orange Group 165B<br>Filament color: Yellow Group 11D<br>Style color: Yellow Group 11D |
| Fragrance | Medium strong fragrance |
| Flowering | Individual flowers last 7-10 days on plant |
| Disease resistance of the plant variety | Slight resistance to Black Spot and Powdery mildew.<br>Downy mildew and Rust not observed on trial plants |
| Distinguishing characteristics from the closest plant varieties | Flower color; distinctive mauve/lilac color, ageing to a slate blue |
| Conditions under which the new cultivar was collected and color readings taken | Outdoors in moderate sunlight |
| Suggested usages | Landscaping and pots |

The foregoing traits have been repeatedly observed and are determined to be among the unique characteristics of 'Pejamblu'. These characteristics distinguish 'Pejamblu' as a new and distinct cultivar:

GENERAL CHARACTERISTICS

A rose of mauve/lilac flower coloring ageing to slate blue, having medium height and compact bushing, with dark green foliage and a strong, pleasant fragrance, with masses of flowers and repeated flowerings from spring to fall.

What is claimed is:

1. A new and distinct variety of Rose plant, substantially as shown and described.

* * * * *